United States Patent [19]

Arai et al.

[11] 4,417,070

[45] Nov. 22, 1983

[54] PROCESS FOR PREPARING AN OPTICAL ACTIVE ESTER OF NAPHTHYLPROPIONIC ACID

[75] Inventors: Kazutaka Arai; Yoshio Ohara; Yasuo Takakuwa; Toyoko Iizumi, all of Funabashi, Japan

[73] Assignee: Nissan Chemical Industries, Ltd., Tokyo, Japan

[21] Appl. No.: 367,044

[22] Filed: Apr. 9, 1982

[30] Foreign Application Priority Data

Apr. 15, 1981 [JP] Japan ................................. 56-731

[51] Int. Cl.³ ............................................. C07B 19/00
[52] U.S. Cl. ..................................... 560/56; 562/401; 562/402
[58] Field of Search ................... 560/56; 562/401, 402

[56] References Cited

U.S. PATENT DOCUMENTS 3,803,245  4/1974  Lodewijk ........................... 560/56 X
3,975,432  8/1976  Alvarez ............................. 560/56 X
3,980,699  9/1976  Fried et al. ....................... 560/56 X Primary Examiner—Natalie Trousof
Assistant Examiner—Vera C. Clarke
Attorney, Agent, or Firm—Frishauf, Holtz, Goodman & Woodward

[57] ABSTRACT

Disclosed is a process for preparing an optical active alkyl ester of α-(6-methoxynaphth-2-yl)propionic acid from the racemic modification thereof or from a mixture of the optical isomers thereof by preferential crystallization. The efficiency of the optical resolution can be increased by adding a base which facilitates the racemization. The process comprises dissolving the racemic modification or the optical isomers in an organic solvent such as methanol, ethanol, etc., with or without a base such as sodium methoxide, sodium ethoxide, etc., and seeding seed crystals of one of the optical isomers to effect crystallization for optical resolution.

11 Claims, No Drawings

PROCESS FOR PREPARING AN OPTICAL ACTIVE ESTER OF NAPHTHYLPROPIONIC ACID

The present invention relates to a novel process for producing an optical active allyl α-(6-methoxynaphth-2-yl)propionate represented by the structural formula

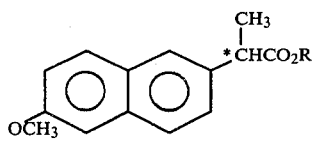

(I)

wherein R is an alkyl group.

Optical active α-(6-methoxynaphth-2-yl)propionic acid obtainable by hydrolyzing the optical active alkyl α-(6-methoxynaphth-2-yl)propionate obtained by the present invention, in retension of the configuration of asymmetric carbon, has strong anti-inflammatory and analgesic activies. Particularly, d-α-(6-methoxynaphth-2-yl)propionic acid is commonly referred to as Naproxen and it is practically used as a pharmaceutical.

For the production of d-α-(6-methoxynaphth-2-yl)propionic acid, there have been known a number of chemical optical resolution methods wherein diastereomer salts are formed with use of optical active bases, as resolving agents, such as an alkaloid (e.g. cinchonidine) (Japanese Patent Publication No. 31981/1974), l-phenethylamine (Japanese Laid-Open Patent Application No. 11284/1978), N-alkyl-D-glucamine (Japanese Laid-Open Patent Application No. 17380/1980), and l-phenylglycine ethyl (Japanese Laid-Open Patent Application No. 15354/1978).

Whereas, the present inventors have developed a novel and simple process wherein the optical resolution can be conducted by preferential crystallization as a physical optical resolution method.

The present inventors attempted firstly to conduct the optical resolution by preferential crystallization with use of several solvents for α-(6-methoxynaphth-2-yl)propionic acid per se. However, poor results were thereby obtained.

Then, the melting points of the racemic modification and the optical active substance of an alkyl α-(6-methoxynaphth-2-yl)propionate were compared, and it was found that the melting points were distinctly different. Further, the solubilities of the racemic modification and the optical active substance were compared with respect to various solvents, and it was thereby found that the optical active substance was more hardly soluble than the racemic modification, i.e. the optical active substance was more readily crystallized than the racemic modification. A part of the data thereby obtained is shown in Table 1.

TABLE 1

The melting points and solubilities of esters of α-(6-methoxynaphth-2-yl)-propionic acid

| Compounds | (Ia) Racemic modification | (Ia) d-form | (Ib) Racemic modification | (Ib) d-form |
|---|---|---|---|---|
| Melting points (°C.) | 65–67 | 91–93 | 50–52 | 81–82 |
| $[\alpha]_D^{20}$ | ±0° | +77–79° | ±0° | +49–51° |
| Solubilities (21° C.) (g/kg) | | | | |
| Methanol | 77 | 33 | — | — |
| Ethanol | — | — | 126 | 38 |
| IPE* | 121 | 53 | 300 | 78 |
| Hexane | 37 | 17 | 70 | 17 |

*IPE: isopropyl ether

On the basis of these data, an extensive study has been made on a process which comprises dissolving in an organic solvent the racemic modification of an alkyl α-(6-methoxynapth-2-yl)propionate or a mixture containing one of the optical isomers in an amount greater than the other, and then seeding pulverized seed crystals of one of the optical isomers to effect the crystallization for optical resolution. And, as a first embodiment of the present invention, a process for preparing an optical active alkyl α-(6-methoxynaphth-2-yl)propionate by a so-called preferential crystallization, has been developed.

Further, on the basis of the discovery that the racemization of the alkyl α-(6-methoxynaphth-2-yl)propionate by means of a base is much faster than that of α-(6-methoxynaphth-2-yl)propionic acid (see Reference Example 1) a second preferred embodiment of the present invention, i.e. a preferential crystallization under racemization, has been developed, wherein the preferential crystallization of the alkyl α-(6-methoxynaphth-2-yl)propionate is conducted in the presence of a base which facilitates the racemization, whereby as the crystallization of one of the optical isomers proceeds, the other optical isomer tending to increase in the mother liquor is racemized and thus the efficiency of the preferential crystallization resolution can substantially be increased.

Namely, the present invention provides a novel process for preparing one of optical isomers of an alkyl α-(6-methoxynaphth-2-yl)propionate from the racemic modification of an alkyl α-(6-methoxynaphth-2-yl)propionate or a mixture containing one of the optical isomers in an amount greater than the other, by means of preferential crystallization or preferential crystallization under racemization.

The optical active alkyl α-(6-methoxynaphth-2-yl)propionate obtained by the process of the present invention can be converted to optical active α-(6-methoxynaphth-2-yl)propionic acid by hydrolysis or by hydrogenation, in retention of the configuration of asymmetric carbon. (see Reference Example 2).

Now, the reaction conditions for the process of the present invention will be described in detail.

Firstly, the racemic modification of an alkyl ester of α-(6-methoxynaphth-2-yl)propionic acid or a mixture containing one of the optical isomers in an amount greater than the other, is dissolved in an organic solvent. As the racemic modification or the mixture of the optical isomers, the intermediate of the process disclosed in U.S. patent application Ser. No. 332,961 filed Dec. 21, 1981 by the present inventors, may be used per se, or the one obtained by any other process may be used. Of course, it is possible to use the one recovered from a filtrate or washing solution obtained as by-products of the process of the present invention.

As the solvent to be used, one providing a greater solubility for the racemic modification than for the optical active substance, is preferred. Accordingly, it is preferred to use, for instance, methanol, ethanol, isopropyl alcohol (IPA), toluene, benzene, hexane, isopropyl ether (IPE) or chloroform. However, solvents which are not directly involved in the reaction, may also be used. The solvents may be used alone or in combination of two or more. In the case where a base is present to conduct the racemization, a solvent having a great polarity such as methanol, ethanol or diethyl formamide is preferred as it facilitates the racemization. However, solvents which are not directly involved in the reaction may also be used. These solvents may be used alone or in combination of two or more.

Then, seed crystals of one of the optical isomers are seeded to effect the preferential crystallization of an optical isomer identical with the seed crystals. The seed crystals of the optical isomer to be added are preferably fine and to have a high optical purity so that crystals having a high purity can be obtained by the preferential crystallization. Accordingly, it is preferred to use seed crystals having an optical purity of at least 90% and finely pulverized e.g. by a mortar.

It is also possible to use the crystals obtained by the process of the present invention as they are. The crystallization may be conducted at a temperature lower than the boiling point of the solvent. However, if the temperature is too high, the amount of the solute increases too much and the viscosity of the solution increases thus leading to difficulties in the separation of the crystals after the crystallization. On the other hand, if the temperature is too low, a great amount of the solvent will be required and the yield of the optical active substance will decrease. Therefore, it is usually preferred to carry out the crystallization at a temperature within a range of from 80° to −10° C.

In the case where the racemization is simultaneously effected, a base such as an alkali metal or alkaline earth metal alkoxide, diazabicycloundecene (DBU), diazabicyclonone (DBN) or a quaternary ammonium alkoxide may be used as the racemization agent. The greater the concentration of the racemization agent is, the faster the racemization reaction proceeds. However, if the amount of the racemization agent is excessively large, the viscosity of the solution tends to increase. In the case of the alkoxides, the amount is preferably from 0.5 to 20% by weight.

In order to efficiently carry out the second embodiment of the present invention, it is important to effectively control the racemization rate and the recrystallization rate. When the racemization rate is slower than the crystallization rate, crystals having an optical activity opposite to that of seed crystals tend to form. In such a case, it is necessary to increase the amount of the racemization agent or to raise the crystallization temperature thereby to increase the racemization rate, and/or to decrease the cooling rate or the degree of supersaturation thereby to lower the crystallization rate. Further, in order to practically effectively conduct this process, it is possible to employ a continuous addition of a solution at a high temperature or a continuous crystallization apparatus.

Now, the present invention will be described in further detail with reference to Examples and Reference Examples.

REFERENCE EXAMPLE 1

Comparison of the racemization rates of α-(6-methoxynaphth-2-yl)propionic acid and its alkyl ester The racemization rates of optical active α-(6-methoxynaphth-2-yl)propionic acid and its methyl ester and its ethyl ester were measured in the following manner.

50 mg of each sample was dissolved in 10 ml of an alcohol solution of sodium alkoxide (RONa/ROH, R=$CH_3$ or $C_2H_5$), and the racemization rate was determined on the basis of a decrease in the optical rotation at a temperature of from 20° to 21° C. The results thereby obtained are shown in Table 2.

TABLE 2

| | Racemization rates | |
|---|---|---|
| Compounds | Conditions for racemization | Racemization rate constants |
| (Ia) 6-methoxynaphthyl-CH(CH₃)CO₂CH₃ | $CH_3ONa/CH_3OH$ Concentration 0.5% (W/W) 2.0% (W/W) | ($sec^{-1}$) $1.5 \times 10^{-5}$ $6.7 \times 10^{-5}$ |
| (Ib) 6-methoxynaphthyl-CH(CH₃)CO₂C₂H₅ | $C_2H_5ONa/C_2H_5OH$ Concentration 2.0% (W/W) | ($sec^{-1}$) $2.9 \times 10^{-4}$ |
| 6-methoxynaphthyl-CH(CH₃)CO₂H | $CH_3ONa/CH_3OH$ Concentration 2.0% (W/W) $C_2H_5ONa/C_2H_5OH$ Concentration 2.0% (W/W) | ($sec^{-1}$) $\leq 2 \times 10^{-7}$ $\leq 2 \times 10^{-7}$ |

It is apparent from Table 2 that the alkyl ester is much more readily racemized than the acid.

EXAMPLE 1

127.4 mg of ethyl dl-α-(6-methoxynaphth-2-yl)propionate was dissolved in 2.54 g of hexane at 30° C., and the solution was cooled to 16.5° C. 9.8 mg of ethyl d-α-(6-methoxynaphth-2-yl)propionate ($[\alpha]_D^{20} = +49.4°$) finely pulverized by an agate mortar was added thereto and the solution was gradually cooled down to 12° C. Crystals formed were collected by filtration, quickly washed with 0.5 ml of hexane and dried, whereupon 15.1 mg of colourless crystals were obtained. The optical rotation of these crystals was found to be $a_D^{20} = +6.5 \pm 0.2°$ (This value should have been $+4.8°$ if the crystals were composed solely of the seed crystals). This clearly indicates an increase of ethyl d-α-(6-methoxynaphth-2-yl)propionate.

For reconfirmation purposes, the filtrate and washing solution were combined and concentrated to obtain 119.9 mg of colourless crystals, and the optical rotation of the colourless crystals were measured to be $a_D^{20} = -1.4 \pm 0.2°$. It was thus confirmed that the optical resolution was effected by the preferential crystallization.

The optical purity was 85.8%, and the amount of the optical active substance increased by 1.3 times over the seed crystals.

EXAMPLE 2

0.965 g of ethyl dl-α-(6-methoxynaphth-2-yl)propionate was dissolved in 8.0 g of ethanol at 30° C., and the solution was then cooled to 20° C. 14.0 mg of ethyl d-α-(6-methoxynaphth-2-yl)propionate ($[\alpha]_D^{20} = +49.4°$) finely pulverized by an agate mortar was added thereto, and the solution was gradually cooled in 18 hours to 9° C. In a manner similar to Example 1, 146 mg of colourless crystals were obtained. The optical rotation was found to be $a_D^{20.5} = +11.5°$ (This value should have been $+6.9°$ if the crystals were composed solely of the seed crystals). The optical purity was 16.0%. The amount increased by 1.7 times over the seed crystals.

EXAMPLE 3

330 mg of ethyl dl-α-(6-methoxynaphth-2-yl)propionate was dissolved in 3.0 ml of an ethanol solution of sodium ethoxide (2.4% (W/W)) at 40° C., and then the solution was cooled down to 20° C. 3.0 mg of ethyl d-α-(6-methoxynaphth-2-yl)propionate ($[\alpha]_D^{20.5} = +48.8°$) pulverized finer than 150 mesh was added, and the solution was slowly cooled in 2 hours to 18° C. The crystals were collected by filtration and quickly washed with 0.5 ml of hexane. Slightly yellow crystals thereby obtained were added to a mixture of 15 ml hydrochloric acid and 20 ml of toluene, subjected to separation, and washed twice with water. Concentration under reduced pressure was followed by drying, whereupon 20.0 mg of colourless crystals were obtained. The optical rotation was $a_D^{20.4} = +9.1°$ (This value should have been $+1.5°$ if the crystals were composed solely of the seed crystals). The optical purity was 92%. The amount increased by 6.1 times over the seed crystals. This indicates that the efficiency of the crystallization for optical resolution was substantially improved by the addition of the base (i.e. sodium ethoxide).

EXAMPLE 4

340 mg of ethyl dl-α-(6-methoxynaphth-2-yl)propionate was dissolved in 3.0 ml of an ethanol solution of sodium ethoxide (3(W/W)) at 50° C., and the solution was cooled down to 23° C. 3.0 mg of ethyl l-α-(6-methoxynaphth-2-yl)propionate ($[\alpha]_D^{20} = -43.8°$) finely pulverized by an agate mortar was added, and the solution was slowly cooled in 4.5 hours to 19° C. Then, the same treatment as in Example 3 was conducted, whereupon 97.3 mg of colourless crystals were obtained. The optical rotation was $a_D^{20.8} = -25.0°$ (This value should have been $-1.3°$ if the crystals were composed solely of the seed crystals). The optical purity was 52%. The amount increased by 19 times over the seed crystals.

EXAMPLE 5

100 mg of methyl dl-α-(6-methoxynaphth-2-yl)propionate was dissolved in 3.0 ml of a methanol solution of sodium methoxide (9.3% (W/W)) at 40° C., and the solution was cooled down to 25.5° C. 1.0 mg of finely pulverized methyl d-α-(6-methoxynaphth-2-yl)propionate ($[\alpha]_D^{20} = +65.1°$) was added, and the solution was slowly cooled in 4.5 hours to 18° C. Then, the same treatment as in Example 3 was conducted, whereupon 24.0 mg of colourless crystals were obtained. The optical rotation was $a_D^{20.8} = +10.5°$ (This value should have been $+0.7°$ if the crystals were composed solely of the seed crystals). The optical purity was 55%. The amount increased by 16 times over the seed crystals.

EXAMPLE 6

330 mg of ethyl dl-α-(6-methoxynaphth-2-yl)propionate was dissolved in 3.0 ml of an ethanol solution of sodium ethoxide (6% (W/W)) at 40° C., and the solution was cooled down to 20° C. 3.0 mg of ethyl d-α-(6-methoxynaphth-2-yl)propionate ($[\alpha]_D^{20} = +48.8°$) pulverized finer than 150 mesh was added, and the solution was slowly cooled in 2.5 hours to 12° C. Then, the same treatment as in Example 3 was conducted, whereupon 93.0 mg of colourless crystals were obtained. The optical rotation was $a_D^{20.4} = +27.1°$ (This value should have been $+1.5°$ if the crystals were composed solely of the seed crystals). The optical purity was 59%. The amount increased by 18 times over the seed crystals.

90 mg of these crystals were recrystallized from 3.5 ml of hexane, whereupon 27 mg of ethyl d-α-(6-methoxynaphth-2-yl)propionate having an optical rotation of $[\alpha_D^{20.4} = +51.1°$ (optical purity of about 100%) was obtained.

EXAMPLE 7

2.0 g of ethyl dl-α-(6-methoxynaphth-2-yl)propionate was dissolved in 4.9 g of an ethanol solution of sodium ethoxide (7.2% (W/W)) at 44° C., and the solution was cooled down to 39° C. 0.03 g of powder of ethyl d-α-(6-methoxynaphth-2-yl)propionate ($[\alpha]_D^{20} = +48.8°$) was added, and the solution was slowly cooled in 6 hours to 32.0° C. Then, the same treatment as in Example 3 was conducted, whereupon 1.45 g of colourless crystals were obtained. The optical rotation was $[\alpha]_D^{20} = +34.7°$ (This value should have been $[\alpha]_D^{20} = +1.0°$ if the crystals were composed solely of the seed crystals).

These crystals were recrystallized from 3.5 g of ethanol, whereupon 1.0 g of ethyl d-α-(6-methoxynaphth-2-yl)propionate having the optical rotation of $[\alpha]_D^{20} = +47.1°$ (optical purity of 96.7%) was obtained. The yield was 48.5%.

EXAMPLE 8

1.60 g of ethyl dl-α-(6-methoxynaphth-2-yl)propionate was dissolved in 4.70 g of an ethanol solution of sodium ethoxide (7.1% (W/W)) at 45° C., and the solution was cooled to 36° C. 0.036 g of powder of ethyl d-α-(methoxynaphth-2-yl)propionate ($[\alpha]_D^{20} = +49.1°$) was added, and the solution was slowly cooled in 9 hours to 25° C. The slurry thereby obtained was portion-wise added to a mixture of 3.88 g of 10% hydrochloric acid and 3.68 g of toluene, and subjected to separation. The toluene layer was washed with water, and then concentrated under reduced pressure, whereupon 1.60 g of slightly yellow crystals were obtained. The optical rotation was $[\alpha]_D^{20} = +31.2°$. These crystals were recrystallized from ethanol with use of 0.01 g of seed crystals, whereupon 1.0 g of ethyl d-α-(6-methoxynaphth-2-yl)propionate was obtained as colourless crystals. The optical rotation was $[\alpha]_D^{20} = +46.2°$ (optical purity of 95%). The yield was 63%.

REFERENCE EXAMPLE 2

150 mg of methyl d-α-(6-methoxynaphth-2-yl)propionate ($[\alpha]_D^{20} = +77.4°$) was dissolved in a mixed solution of 3.0 g of formic acid, 0.3 g of water and 0.3 g of concentrated sulfuric acid, and the solution was heated at 40° C. for 6 hours. Water was added thereto, and the solution was extracted with a mixture of toluene and ethylacetate. The organic extracts were combined, and extracted three times with an aqueous sodium hydroxide solution. The organic layer was concentrated, and 60.1 mg of the starting material was thereby recovered. The alkaline layer was acidified with 10% hydrochloric acid, extracted with ethyl acetate and concentrated under reduced pressure, whereupon 89.2 mg of d-α-(6-methoxynaphth-2-yl)propionic acid was obtained as colourless crystals. The yield was 63%. The optical rotation was $[\alpha]_D^{20} = +58.9°$ and the optical purity was 88%.

m.p.; 156° to 157° C.

NMR (CDCl$_3$) δ; 1.57 (3H, d, 7 Hz), 3.83 (1H, q, 7 Hz), 3.86 (3H, s), 6.9–8.0$_5$ (6H, m), 8.0 (1H, broad s)

IR (KBr); 2930, 1690, 1595, 1380, 1260, 1223, 1027, 920, 853, 820, 673, 480 cm$^{-1}$

MS(m/e); 230 (93, M+), 185 (100)

We claim:

1. A process for preparing an optical active alkyl ester of α-(6-methoxynaphth-2-yl)propionic acid, which comprises dissolving in at least one organic solvent which is not directly involved in the reaction a racemic modification of an alkyl ester of α-(6-methoxynaphth-2-yl)propionic acid or a mixture containing one of the optical isomers in an amount greater than the other, and seeding seed crystals of one of the optical isomers to effect crystallization for optical resolution.

2. The process as claimed in claim 1, wherein the crystallization for optical resolution is carried out in the presence of a base selected from the group consisting of alkali metal alkoxides, alkaline earth metal alkoxides, diazabicycloundecene, diazabicyclononene and quaternary ammonium alkoxides.

3. The process as claimed in claim 1 or 2, wherein the organic solvent is selected from the group consisting of methanol, ethanol, isopropyl alcohol, toluene, benzene, hexane, isopropyl ether and chloroform.

4. The process as claimed in claim 3, wherein the organic solvent is selected from the group consisting of methanol, ethanol and diethylformamide.

5. The process as claimed in claim 1 or 2, wherein the seed crystals are finely pulverized crystals having an optical purity of at least 90%.

6. The process as claimed in claim 1 or 2, wherein the crystallization for optical resolution is carried out at a temperature within a range of from 80° to −10° C.

7. The process as claimed in claim 2, wherein the base is an alkoxide and is present in the system of crystallization for optical resolution in an amount of from 0.5 to 20% by weight.

8. A process for preparing an optical active alkyl ester of α-(6-methoxynaphth-2-yl)propionic acid, which comprises dissolving in at least one organic solvent selected from the group consisting of methanol, ethanol, isopropyl alcohol, toluene, benzene, hexane, isopropyl ether and chloroform, a racemic modification of an alkyl ester of α-(6-methoxynaphth-2-yl)propionic acid or a mixture containing one of the optical isomers in an amount greater than the other in the presence of a base selected from the group consisting of alkali metal alkoxides, alkaline earth metal alkoxides, diazobicycloundecene, diazabicyclononene and quaternary ammonium alkoxides and seeding finely pulverized seed crystals having an optical purity of at least 90% of one of the optical isomers at a temperature within the range of from 80° C. to −10° C. to effect crystallization for optical resolution.

9. The process as claimed in claim 8 wherein the base is an alkoxide and is present in the system of crystallization for optical resolution in an amount of from 0.5 to 20% by weight.

10. The process as claimed in claim 1 wherein said solvent is selected from those providing greater solubility for said racemic modification than for the optical isomers.

11. The process as claimed in claim 2 wherein said solvent is selected from those providing greater solubility for said racemic modification than for the optical isomers.

* * * * *